United States Patent [19]

Tsay

[11] Patent Number: 4,981,951

[45] Date of Patent: Jan. 1, 1991

[54] LECTIN AFFINITY CHROMATOGRAPHY OF FACTOR VIII

[75] Inventor: Grace C. Tsay, Walnut Creek, Calif.

[73] Assignee: Miles Inc., Elkhart, Ind.

[21] Appl. No.: 181,001

[22] Filed: Apr. 14, 1988

[51] Int. Cl.$^5$ ............................ C07K 3/18; C07K 3/20
[52] U.S. Cl. .................... 530/383; 530/395; 530/413; 530/417; 530/415
[58] Field of Search ............... 530/383, 397, 395, 396, 530/413, 417

[56] References Cited

U.S. PATENT DOCUMENTS 4,341,754  7/1982  Kaplan et al. ........................ 424/1
4,886,747  12/1989  Derynck et al. ................... 435/69.4

Primary Examiner—Margaret Moskowitz
Assistant Examiner—Keith C. Furman
Attorney, Agent, or Firm—David J. Aston; Bertram Bradley

[57] ABSTRACT

A method of purifying a recombinant protein from a solution, such as tissue culture fluid, containing gylcoproteins. The affinity of lectins for specific glycoproteins is assessed and used to select a particular lectin specific for the contaminating glycoprotein(s). A sugar buffer such as alpha methyl mannoside prevents binding of the recombinant protein. The preferred lectin is lentil lectin, for use in separating recombinant Factor VIII from tissue culture fluid contaminated with rodent protein from the cell line used to produce the recombinant Factor VIII.

6 Claims, No Drawings

LECTIN AFFINITY CHROMATOGRAPHY OF FACTOR VIII

BACKGROUND OF THE INVENTION

1. Field of the Invention

The present invention relates to the purification of proteins, and, more particularly, to the purification of clotting Factor VIII:C by means of affinity chromatography.

2. Related Art

It is known that the clotting of human blood is a complicated process, involving a series of reactions mediated by 13 different factors. The cause of hemophilia A is the inability of the afflicted individual to synthesize one of these factors, known variously as antihemophilic factor, AHF, AHG, Factor VIII or Factor VIII:C, in amounts sufficient to support adequate clotting. About 40 percent of hemophiliac have no ability to synthesize AHF, while the others have diminished ability. Dried preparations of AHF concentrate are sold commercially for administration to hemophiliacs for treatment of bleeding or in advance of surgery. The AHF concentrate is obtained from plasma from human donors, through the use of known techniques. At the time of use, the dried concentrate is dissolved in sterile water, and the resulting solution is administered intravenously.

AHF concentrate contains a Factor VIII complex which consists of at least two components, one of which is called Factor VIII:C, in which C means that this component is responsible for the coagulation activity of the complex in the reaction chain. This component is considered to contain the antigen, as shown by means of antibodies, which are developed in certain persons suffering from hemophilia and which prevent the coagulation activity of Factor VIII:C. The antigen is called F.VIII:CAG. The other component has been called Factor VIII:RAG or F.VIII-related antigen. This antigen is different from the antigen F.VIII:CAG. The Factor VIII:C and the (antigen) Factor VIII:CAG are lacking in hemophilia of type A in a serious form. In this disease there is a normal content of Factor VIII:RAG. In von Willebrand's disease, there is a lack of Factor VIII:RAG in the blood and a corresponding lack of Factor VIII:C. For persons suffering from a serious form of von Willebrand's disease the lack of Factor VIII:RAG is almost total and the content of Factor VIII:C is about 5% of the normal content. In von Willebrand's disease, the activity of the so-called Factor VIII:RCF is highly reduced.

In November, 1984, the cloning of Factor VIII:C was reported by two groups. (Vehar et al., Nature, 312:337-342 (1984); Gitschier et al., Nature, 312:326-330 (1984); Toole, et al., Nature, 312:342-347 (1984)).

Both groups used similar methods for the DNA cloning and expression of Factor VIII:C. Oligonucleotide probes were synthesized on the basis of small sections of the amino acid sequence of purified Factor VIII:C (either porcine or human in origin), and used to screen an appropriate library of genomic clones to identify part of the Factor VIII:C gene. The gene itself turned out to be extraordinarily long.

For expression of protein, it was necessary to isolate cDNA clones. These were obtained either from a human T-cell hybridoma line (Genentech) or from human liver (Genetics Institute) and sequence analyses allowed the derivation of the entire 2,332 amino acid sequences of the mature protein. Both groups note that the protein is highly glycosylated and has an obvious domain structure with predictable homology to another clotting factor, Factor V, but also an unpredicted homology to ceruloplasmin—a serum protein believed to be involved in copper ion transport in the blood. The protein sequence also allows the definition of the main sites that are cleaved by thrombin in the process of activation of Factor VIII:C.

The expression of Factor VIII:C in mammalian cells required the reconstruction of a full length cDNA clone and its attachment to a viral promoter sequence. When this construction was introduced into either a hamster kidney cell (BHK) (Genentech) or a monkey kidney cell line (COS) (Genetics Institute), a human Factor VIII:C-like activity was secreted into the media in which the cells were grown. The concentrations of Factor VIII:C-like activity in the media were about one percent (Genetics Institute) or seven percent (Genentech) of the normal plasma concentration as assayed by a sensitive biochemical test based on the activation of Factor X and hydrolysis of a chromogenic substrate. Factor VIII activity is measured either by the chromogenic assay as the coagulation assay. In both instances, a WHO-accepted reference standard is used, and the results are reported in international units (IU) wherein 1 unit represents the Factor VIII activity in 1 ml of normal plasma. One mg of pure F.VIII is estimated to correspond to approximately 4500 IU. Both groups showed that the secreted activity (further purified by affinity chromatography at Genentech) was able to correct the clotting time of plasma from a hemophiliac. Evidence that these assays are indeed a measure of Factor VIII:C and not of some other clotting factor or non-specific activity, was provided by additional tests carried out by both groups.

The above-described cloning at Genentech is also described in EPO No. 0 160 457.

The purification described in Nature 312:337-338, supra, involved fractionation of proteins by TSK 4000 HPLC, and HPLC chromatography. Since these were analytical techniques, there is no discussion in the reference of the purities obtained by these techniques.

The cloning and expression of recombinant Factor VIII has subsequently been reported by other researchers. For example, Sarver et al., DNA 6(6):553-564 (1987), report purification of rF.VIII using an immobilized monoclonal antibody to VIII:C.

However, published information on the purification of rF.VIII is, at best, limited.

Various chromatography purification techniques have also been applied to plasma-derived Factor VIII.

Zimmerman et al., Re. No. 32,011, disclose a method of preparing high purity Factor VIII either from a commercially available Factor VIII concentrate or from porcine plasma. The process involves, as the first step, the immunoadsorption of F.VIII/vWF onto murine, a monoclonal antibody specific for vWF. The Factor VIII is then eluted with a calcium chloride solution (0.01M to 0.03M) and then concentrated with an aminohexyl agarose column.

The Factor VIII thus produced is described as having a specific activity of around 2300 when prepared from a Factor concentrate and being free substantially of von Willebrand Factor.

Various other methods using affinity chromatography have been described for concentrating Factor VIII from plasma. Andersson, EP No. 197901, discloses a method for preparing fragments of AHF using immunoaffinity chromatography followed by HPLC on an anion-exchange adsorbent. The anion exchange adsorbent may be Mono Q gel or TSK DEAE 5 PW gel. Fragments are then obtained by incubation with thrombin.

Johnson, U.S. Pat. No. 4,397,841, discloses preparation of Factor VIII:C by fractionation of plasma with a sequence of adsorption steps employing polyelectrolyte copolymers in the presence of heparin. A suitable resin is a copolymer of ethylene and maleic anhydride.

Other methods using affinity techniques in the downstream processing of plasma-derived and recombinant proteins are discussed in Lowe, *J. Biotechnology*, 1:3–12 (1984). None of the methods discussed use lectins.

Lectins have been hitherto used in the analysis of carbohydrate portions of glycoproteins. Kornfeld et al., *J. Biol. Chem.*, 256:6633–6640 (1981), disclose the carbohydrate-binding specificity of pea and lentil lectins. Labelled human IgG immunoglobulins were passed over various lectin-Sepharose columns. The fractionation pattern was then compared to the known glycosylation pattern.

In *J. Biol. Chem.*, 257:11230–11234 (1982), Cummings et al. report that various hemaglutinin lectins can be used to distinguish various Asn-linked oliogosaccharides with different branching patterns. This was used to separate glycopeptides prepared from bovine thyroglobulin.

The differentiation of ribonucleases from different human organs has also been studied by the fractionation of various ribonuclease preparations on lectin-affinity columns. Each lectin column used showed a different binding pattern for each ribonuclease studied, demonstrating that the various ribonucleases have different glycosylation patterns.

This review of the prior art suggests that lectin chromatography has not been previously used in the recovery or isolation of proteins, whether plasma-derived or of recombinant origin.

SUMMARY OF THE INVENTION

The present invention comprises the use of immobilized lectins in the presence of a sugar solution for the selective removal of contaminating proteins from recombinant Factor VIII. By virtue of the present method, there is prepared a purified recombinant Factor VIII (rF.VIII) which is safe for human administration. This principle could easily be applied to other biotechnology products produced in mammalian cell culture.

Selective fractionation of rF.VIII is accomplished through the use of a sugar buffer which prevents binding of the rF.VIII to the lectin. The lectin is chosen to have a high binding affinity for the contaminating protein.

In the preferred embodiment, alpha-methyl-mannoside is used in the buffer solution and lentil lectin is used to adsorb hamster protein.

DESCRIPTION OF THE PREFERRED EMBODIMENT

The present invention has been carried out with "rF.VIII concentrates", which are partially purified preparations obtained from a hamster cell line, which has been transfected with an expression vector comprising DNA encoding Factor VIII, as described in European patent application Publication No. 0 160 457, Nov. 6, 1985, the description of which is hereby incorporated by reference. Tissue culture fluid containing rF.VIII is subjected to partial purification to obtain the rF.VIII concentrate. This purification is not critical to the present invention, and may be carried out, for example, as described at p. 61 of EPO No. 0 160 457, wherein the serum-containing media containing Factor VIII activity was chromatographed on a column containing an anti-Factor VIII monoclonal antibody. The following examples were carried out with rF.VIII concentrate obtained from cells which were grown in a medium which did not contain serum, having instead human serum albumin and other human proteins added to the growth medium, as well as other standard nutrients such as bovine insulin, transferrin, etc. The cell-free harvest was concentrated, passed over a diethylaminoethyl (hereinafter DEAE) DEAE column and chromatographed on a column containing an anti-Factor VIII antibody to obtain the present concentrate. Thus, the material to be purified using the present process contained one major protein contaminant of interest, BHK. The following is a particular description of the present source of rF.VIII concentrate:

(a) rF.VIII is separated from tissue culture fluid by centrifugation or by filtration at 4° C. for not more than 48 hours.

(b) The rF.VIII is absorbed onto DEAE-SEPHAROSE manufactured by pharmacia, see 1987 pharmacia catalog. The DEAE-SEPHAROSE is washed with 10 volumes of equilibration buffer (0.02M imidazole, 0.01M CaCl$_2$, 0.05M NaCl, pH 6.9) and eluted with 0.02M imidazole, 0.01M CaCl$_2$, 0.25M NaCl, pH 6.9.

(c) The DEAE eluate has NaCl added to bring it to 0.3M NaCl, glycerol added to 10%, and Tween 80 added to 0.01%. DEAE-SEPHAROSE equilibrated in 0.02M imidazole, 0.01M CaCl$_1$2, 0.3M NaCl, 10% glycerol, 0.01% TWEEN 80 (a complex mixture of polyoxyethylene ethers of mixed partial oleic esters of sorbitol anhydrides, Merck Indus., eighth edition 1968), pH 6.9 is added (10% [w/v]). The slurry is mixed for not less than 1 hour and then the solution is separated from the DEAE by filtration and frozen at −35° C.

(d) The F.VIII is thawed and chromatographed on murine monoclonal Ab to F.VIII. The columns are washed with 0.02M imidazole, 0.01M CaCl$_2$, 0.7M NaCl, pH 6.9 and eluted with 0.02M imidazole, 1.0M CaCl$_2$, 0.7M NaCl, 0.01% TWEEN 80, pH 6.9.

(e) This eluate is diafiltrated and ultrafiltrated against 0.02M imidazole, 0.3M NaCl, 0.01M CaCl$_2$, pH 6.9.

The following Examples were carried out with the following materials: Concanavalin A were obtained from Pharmacia SEPHAROSE, wheat germ lectin-SEPHAROSE, and lentil-lectin SEPHAROSE α-Methylmamoside, and N-acetylglucosamine were purchased from Sigma.

As used generally herein, the term "lectin" means protein or glycoprotein substances, usually of plant origin, that bind to sugar moieties in cell walls or membranes and thereby change the physiology of the membrane to cause agglutinotein, mitosis or other biochemical changes in the cell.

Generally, a lectin is selected which selectively binds the major contaminating protein of interest, e.g. BHK. "BHK" protein is thought to consist generally of cellular protein, and, as such, the protein contaminants from this particular cell line will be the same as the contaminants from other rodent cell lines, such as CHO, murine hybridomas, etc.

EXAMPLE 1 rF.VIII concentrate was treated with three different immobilized lectins:

Both Factor VIII activity (as measured by coagulation assay) and BHK protein (as measured by ELISA) were partially adsorbed to the SEPHAROSE-bound lectins (Concanavalin A, wheat germ lectin, lentil lectin) in various dilutions.

The mixtures of rF.VIII concentrate: lectin-SEPHAROSE were rotated at 4° C. for 18 hours. The slurry was then placed in a disposable column and flow-through measured. Elution was then carried out with 0.5M α-methyl-mannoside (α-MM), 0.5M N-aetyl-gluosamine (GlcNac) in 0.02M imidazole 0.3M NaCl, 0.01M Cacl$_2$, pH6.9.

Both α-M-M and 0.5M (GlcNAc) were used as buffer solutions because α-M-M has been shown previously to elute glycopeptides from pea lectin or lentil lectin agarose. (See Kornfeld, et al., supra, and Cowan et al., *J. Biol. Chem.* 257(19): 11241–11248 (1982)). GlcNac is known also to dissociate certain glycoproteins from lectins, e.g., wheat germ lectin (See, for example, Cummings et al., supra.)

Only about 10–30% of the starting Factor VIII activity could be eluted from the immobilized lectins. This indicates that there is no purified rFVIII in either the flow through or the eluate fractions from a column made using these materials. The results from this preliminary experiment are shown below in Table 1.

TABLE 1

| | Test | VIII:C Activity (u/ml) | BHK (ng/ml) | VIII:C Activity Yield (%) |
|---|---|---|---|---|
| 1. | F.VIII concentrate + 0.5 M α-M-M buffer | >34 | 47.2 | 100 |
| 2. | F.VIII concentrate + 0.5 M GlcNAc buffer | >34 | 53.5 | 100 |
| 3. | F.VIII concentrate + lentil lectin (3:1 v/v) Flowthrough (Vol. 0.6 ml) | 1.33 | 1.86 | 3.5 |
| 4. | 0.5 M α-M-M eluate, 0.6 ml from #3 | >17 | 15.4 | 28.8 |
| 5. | F.VIII concentrate + wheat germ lectin (4:1 v/v) Flowthrough (Vol. 0.6 ml) | 7.8 | 7.4 | 13.8 |

TABLE 1-continued

| | Test | VIII:C Activity (u/ml) | BHK (ng/ml) | VIII:C Activity Yield (%) |
|---|---|---|---|---|
| 6. | 0.5 GlcNAc eluate from #5, 0.6 ml. | >17 | 18.2 | 34.0 |
| 7. | F.VIII concentrate + wheat germ lectin (30:1 v/v) Flowthrough (Vol. 0.3 ml) | >17 | 44.4 | 83.0 |
| 8. | 0.5 M GlcNAc eluate, from #7, 0.3 ml | 12.1 | 8.0 | 15.0 |
| 9. | F.VIII concentrate + ConA (30:1 v/v) Flowthrough (Vol. 0.6 ml) | >17 | 26.3 | 49.2 |
| 10. | 0.5 M α-M-M eluate from #9, 0.3 ml | >8.5 | 5.8 | 10.8 |

In Table 1, lines 1 and 2 are controls. Lines 3 and 4 show that both BVHK and rF.VIII were moderately bound to lentil lectin. Lines 5–10 show similar results with other lectins.

EXAMPLE 2

Different lectins are known to have different carbohydrate binding specificities. For example, as discussed by Kornfeld et al., supra, the presence of a fucose residue attached to the asparagine linked to N-acetyl glycosamine residues of the glycoprotein is essential for high affinity binding to lentil lectin-SEPHAROSE but not to Concanavalin A SEPHAROSE. In addition to fucose, 2-α-mannose residues are required for glycoprotein binding to lentil lectin-SEPHAROSE but not with those in which 1-α-mannose is substituted at C2 and C4. Wheat germ lectin-SEPHAROSE (WGA) specifically binding to N-acetyl glycosamine residues of glycoprotein.

The present process results in separation of BHK glycoprotein from rF.VIII immobilized lectins. Both glycoproteins have different carbohydrate specificity binding to lentil lectin, WGA, and ConA. The presence of 0.5M α-methyl mannoside (α-M-M) can prevent low affinity binding glycoprotein (rF.VIII) from binding to lentil lectin-SEPHAROSE but high affinity binding glycoprotein (BHK protein) still can bind to lentil lectin-SEPHAROSE.

Table 2 below shows results when rF.VIII concentrate was rotated at 4° C. overnight in the presence of 0.5M α-MM or 0.5M GlcNAc plus different lectins. The materials were then rotated at room temperature and spun down. Assays were performed on the supernatant.

TABLE 2

| | Test | VIII:C (u/ml) | BHK (ng/ml) | BHK VIII:C (ng/u) | BHK Reduction (%) | Yield (%) |
|---|---|---|---|---|---|---|
| 1. | rF.VIII:C + buffer control | ND | — | — | — | — |
| 2. | rF.VIII:C + buffer control (α-M-M) | 19.6 | 41.2 | 2.1 | — | 100 |
| 3. | rF.VIII:C + buffer control (GlcNAc) | 20.8 | 38.6 | 1.9 | — | 100 |
| 4. | rF.VIII:C + buffer control | 112,1, 113 | 55.4 | 0.43 | — | — |
| 5. | rF.VIII:C + buffer control (α-M-M) | 139.2, 97.0 | 57.6 | 0.41 | — | 100 |
| 6. | rF.VIII:C + buffer control (GlcNAc) | 105.4 | 37.8 | 0.36 | — | — |
| | rF.VIII:C + α-M-M + lentil lectin | | | | | |

TABLE 2-continued

| Test | VIII:C (u/ml) | BHK (ng/ml) | BHK VIII:C (ng/u) | BHK Reduction (%) | Yield (%) |
|---|---|---|---|---|---|
| 7. (2:2:1) | 19.3 | 14.8 | 0.76 | 63.8 | 95.5 |
| 8. (1:1:1) | 18.0 | 13.2 | 0.73 | 65.2 | 89.1 |
| 9. (2:2:1) | 101.3 | 12.0 | 0.12 | 72.1 | 90.4 |
| 10. (1:1:1) | 93.9 | <7.5 | <0.08 | >80.5 | 83.8 |
| 11. (2:3:1) | 107.4 | 11.7 | 0.11 | 74 | 95.8 |
| 12 (2:3:2) | 122.2 | <8.8 | <0.07 | >82.3 | 109 |
| rF.VIII:C + GlcNAc + WGA | | | | | |
| 13. (2:2:1) | 6.8 | 31.5 | 4.6 | Non-reduction | 33.7 |
| 14. (4:4:1) | 13.3 | 38.9 | 2.9 | Non-reduction | 65.8 |
| 15. (2:2:1) | 58.5 | 32.0 | 0.54 | Non-reduction | 52.2 |
| 16. (4:4:1) | 71.8 | 33.1 | 0.46 | Non-reduction | 64.0 |
| 17. (1:2:1) | 79.2 | 24.0 | 0.30 | Non-reduction | 70.7 |
| rF.VIII:C + α-M-M + ConA | | | | | |
| 18. (2:2:1) | 87.3 | 8.3 | 0.09 | 79 | 77.9 |
| 19. (2:1:1) | 69.2 | 9.6 | 0.14 | 67 | 61.7 |
| 20. (2:3:1) | 89.4 | 15.3 | 0.17 | 60 | 79.8 |
| 21. (4:4:1) | 106.9 | 16.2 | 0.15 | 65 | 95.4 |

As shown, rF.VIII concentrate in the presence of 0.5M α-methyl mannoside, contacted with Concanavalin A-SEPHAROSE resulted in only 65–79% BHK reduction.

In this Example, in the presence of 0.5M N-acetyl glycosamine, both BHK proteins and rF.VIII concentrate did not bind to WGA and caused no BHK protein reduction. Thus, lentil lectin-SEPHAROSE is the best candidate in the presence of 0.5M α-methyl mannoside to absorb BHK protein.

Table 2 indicates that lentil lectin results in 83.8–100% of Factor VIII activity remaining in the supernatant and 63.8 to 80.5% BHK being bound to the lentil lectin.

EXAMPLE 3

Three lots of rF.VIII concentrate (15 ml) in the presence of 0.5M α-M-M (15 ml) and lentil lectin-SEPHAROSE (11.25 ml) were rotated at 4° C. overnight then poured on disposable columns. Unbound materials were collected and the column was washed with 0.25M α-M-M (15 ml). The flow through and wash fractions were combined together and passed through a second MAb affinity column to provide highly purified rF.VIII. These results indicate that in MAb eluate after lentil lectin absorption, BHK protein reduction was about 88% (7.6-fold reduction) with Factor VIII recovery being 84% (average). These results match the previous small scale study.

TABLE 3

| | Test | Volume ml | VIII:C u/ml | Yield % | BHK ng/ml | BHK* ng/4500 |
|---|---|---|---|---|---|---|
| 1. | rF.VIII:C | 15 | 60.9 | 100 | 77.6(56.7) | 5734 |
| | Lentil lectin-SEPHAROSE | 41.2 | 19.4 | 87 | 2.17(2.9) | 503 |
| | MAb eluate | 16.9 | 33.6 | 62 | 1.84(<1.0) | 282(<134) |
| ii. | rF.VIII:C | 15 | 81.3 | 100 | 65.1(66) | 3602 |
| | Lentil lectin-SEPHAROSE | 40 | 29.2 | 96 | 3.37(3.8) | 519 |
| | MAb eluate | 20.8 | 35.6 | 61 | <0.3(<1.0) | <40(<134) |
| iii. | rF.VIII:C | 15 | 114 | 100 | 151.2 | 5968 |
| | Lentil lectin-SEPHAROSE | 41.3 | 28 | 68 | 7.9 | 1270 |
| | MAb eluate | 21.3 | 51.7 | 64 | 3.1 | 337 |

*Values account for volume increase across dialysis.

The preceding examples illustrate the principle features of the present invention. Using these examples, one skilled in the art could, with routine experimentation, adapt the present invention to other embodiments. For example, the mannoside buffer could range between from 0.3M to 0.5M without varying experimental conditions. The protein to be purified could easily range from 60 to 200 u/ml concentration in the concentrate, termed herein rF.VIII concentrate. The concentrate could contain other recombinant glycoproteins. The affinity of such proteins could be determined by the methods disclosed herein. Thus, the present invention should be understood to be defined, not by the preferred embodiment, but by the lawful scope of the appended claims.

What is claimed is:

1. A method of purifying a Factor VIII recombinant protein from a solution containing contaminating glycoproteins comprising:
    (a) selecting a lectin which adsorbs said glycoproteins;
    (b) immobilizing said lectin on a support to form an immobilized lectin;
    (c) selecting a sugar contained in a buffer wherein said sugar prevents adsorption of said protein onto said immobilized lectin;
    (d) contacting said solution with said immobilized lectin in the presence of said sugar; and
    (e) separating said Factor VIII protein from a said support containing said lectin and said contaminating glycoproteins.

2. The method of claim 1 wherein said sugar is alpha-methyl mannoside.

3. The method of claim 1 wherein said sugar is contained in a buffer solution in an amount of between 0.3M to 0.5M.

4. The method of claim 1 wherein said lectin is selected from the group consisting of lentil lectin and concanavalin A.

5. The method of claim 1 wherein said glycoproteins are rodent glycoproteins.

6. The method of claim 5 wherein said lectin is lentil lectin.

* * * * *